United States Patent
Gibboni et al.

Patent Number: 5,518,891
Date of Patent: May 21, 1996

[54] DYE FORMING COMPOSITION AND DETECTION OF HYDROGEN PEROXIDE THEREWITH

[75] Inventors: David J. Gibboni, Havertown, Pa.; Viktor G. Kartsev, Chernogolovka, Russian Federation; Alexander G. Ignotenko, Donetsk, Ukraine; Alexei Sukhotin, Chernogolovka, Russian Federation

[73] Assignee: Actimed Laboratories, Inc., Burlington, N.J.

[21] Appl. No.: 111,490

[22] Filed: Aug. 25, 1993

Related U.S. Application Data

[63] Continuation-in-part of Ser. No. 37,120, Mar. 25, 1993, abandoned.

[51] Int. Cl.$^6$ .............................. C12Q 1/28; C12Q 1/60
[52] U.S. Cl. ........................... 435/28; 435/11; 435/810; 436/904
[58] Field of Search ......................... 435/28, 10, 11, 435/14, 805, 810; 436/71, 95, 135, 808, 904

[56] References Cited

U.S. PATENT DOCUMENTS

| | | | |
|---|---|---|---|
| 3,770,381 | 11/1973 | Schmitt et al. | 23/230 B |
| 3,986,833 | 10/1976 | Mast et al. | 23/230 B |
| 4,071,317 | 1/1978 | Lam | 23/253 TP |
| 4,071,318 | 1/1978 | Lam | 23/253 TP |
| 4,071,321 | 1/1978 | Lam | 23/253 TP |
| 4,089,747 | 5/1978 | Bruschi | 195/99 |
| 4,101,381 | 7/1978 | Klose et al. | 195/99 |
| 4,119,405 | 10/1978 | Lam | 422/56 |
| 4,247,297 | 1/1981 | Berti et al. | 23/230 B |
| 4,247,631 | 1/1981 | Nix | 435/10 |
| 4,251,629 | 2/1981 | Yamanisi | 435/28 |
| 4,260,679 | 4/1981 | Tsuda | 435/10 |
| 4,321,397 | 3/1982 | Nix | 548/366 |

(List continued on next page.)

Primary Examiner—Ralph J. Gitomer
Attorney, Agent, or Firm—Iver P. Cooper

[57] ABSTRACT

A color-forming coupler is provided which can be used in test compositions, as well as methods and apparatus for detection of hydrogen peroxide. The color-forming coupler compounds react with a hydrazone or an aminoantypyrine in the presence of peroxidase and hydrogen peroxide to produce a darkly colored compound. In the presence of peroxidase and hydrogen peroxide, the couplers of the present invention react with a hydrazone or an aminoantipyrine to produce a deeply colored dye, which can be used to give a visual indication of the analyte present in the sample. These couplers can be used in diagnostic tests in which the analyte is converted to hydrogen peroxide. The color-forming couplers are N,N-disubstituted anilines of the formula shown in FIG. 1, wherein $R^1$ and/or $R^2$=H, $C_1$–$C_9$ alkyl, $C_1$–$C_9$–$C_9$ alkoxy, $NR^3R^4$ (where $R^3$ and/or $R^4$=H, $C_1$–$C_9$ alkyl, aryl, or heteroryl), F, Cl, Br, I, $COOR^5$ (where $R^5$= H, $C_1$–$C_9$ alkyl, aryl, or heteroaryl), CN, $CONR^6R^7$ (where $R^6$ and/or $R^7$= H, $C_1$–$C_9$ alkyl, aryl, or heteraryl), aryl, aryloxy, heteroaryl, heteroaryloxy; and $R^{11}$, $R^{12}$, $R^{13}$, and/or $R^{14}$= H, $C_1$–$C_9$ alkyl, $C_1$–$C_9$ alkoxy, or $NR^{15}R^{16}$ wherein at least one of $R^{11}$ and $R^{14}$ is $NR^{15}R^{16}$ wherein only one of $R^{11}$ and $R^{14}$ is H or $C_1$–$C_2$ alkyl; where $R^{15}$ and/or $R^{16}$= H, $C_1$–$C_9$ alkyl, aryl, or heteroaryl, F, Cl, Br, I, $COOR^{17}$, where $R^{17}$= H, $C_1$–$C_9$ alkyl, aryl, or heteroaryl, CN, $CONR^{18}R^{19}$ (where $R^{18}$ and/or $R^{19}$= H, $C_1$–$C_9$ alkyl, aryl, or heteroaryl, aryl, aryloxy, heteroaryl, heteroaryloxy; and n=0–10 and m=0–10 and

Z and/or y= H, OH, SH, $COOR^8$ (where $R^8$=H, $C_1$–$C_9$ alkyl, aryl, or heteroaryl), CN, $NR^9R^{10}$ (where $R^9$ and/or $R^{10}$= H, $C_1$–$C_9$ alkyl, aryl, or heteroaryl), $NR^{20}NHR^{21}$ (where $R^{20}$ and/or $R^{21}$=H, $C_1$–$C_9$ alkyl, aryl, or heteroaryl), where at least one of Z or Y is $COOR^8$, CN $NR^9R^{10}$, or $NR^{20}NHR^{21}$ or 4-amino antipyrines.

32 Claims, 3 Drawing Sheets

| Structure | Abbrev. | Name |
|---|---|---|
| Phenyl-N(CH$_2$COOH)$_2$ | PAGA | N,N-(biscarboxymethyl)aniline |
| MeO-Phenyl-N(CH$_2$COOH)$_2$ | MOPAGA | N,N-(biscarboxymethyl)-4-methoxyaniline |
| Phenyl-N(CH$_2$CH$_2$COOH)$_2$ | PAPA | N,N-(bis-β-carboxyethyl)aniline |
| Phenyl-N(Et)(CH$_2$COOH) | EPG | N-ethyl-N-phenylglycine |

U.S. PATENT DOCUMENTS

| | | | |
|---|---|---|---|
| 4,418,037 | 11/1983 | Katsuyama | 422/56 |
| 4,439,527 | 3/1984 | Parebusch | 436/135 |
| 4,492,754 | 1/1985 | Trager | 435/28 |
| 4,670,385 | 6/1987 | Babb | 435/28 |
| 4,672,029 | 6/1987 | Washburn | 435/10 |
| 4,737,457 | 4/1988 | Evans et al. | 435/14 |
| 4,820,632 | 4/1989 | Frey | 435/7 |
| 4,954,445 | 9/1990 | Yoshihama | 435/191 |
| 4,966,855 | 10/1990 | Deneke et al | 436/66 |
| 4,971,918 | 11/1990 | Bouse et al. | 436/166 |
| 5,102,778 | 4/1992 | Nakamura | 430/393 |
| 5,126,247 | 6/1992 | Palmer | 435/25 |
| 5,234,818 | 8/1993 | Zimmermann | 435/28 |
| 5,238,818 | 8/1993 | Hashizume | 435/28 |

| | | |
|---|---|---|
| PAGA | N,N-(biscarboxymethyl)aniline | |
| MOPAGA | N,N-(biscarboxymethyl)-4-methoxyaniline | |
| PAPA | N,N-(bis-β-carboxyethyl)aniline | |
| EPG | N-ethyl-N-phenylglycine | |

5,518,891

DYE FORMING COMPOSITION AND DETECTION OF HYDROGEN PEROXIDE THEREWITH

This application is a continuation-in-part of Serial No. 08/037,120, filed Mar. 25, 1993 now abandoned.

BACKGROUND OF THE INVENTION

1. Field of the Invention

The present invention relates to a color-forming coupler which can be used in test compositions, methods and apparatus for detection of hydrogen peroxide. In the presence of peroxidase and hydrogen peroxide, the couplers of the present invention react with a hydrazone or an aminoantipyrine to produce a deeply colored dye, which can be used to give a visual indication of the analyte present in the sample. These couplers can be used in diagnostic tests in which the signal producing system generates hydrogen peroxide as a measure of the analyte present.

2. Description of the Background Art

The detection and quantitative determination of hydrogen peroxide, and compounds capable of reacting to form hydrogen peroxide, are important in many areas. For example, hydrogen peroxide is produced in the enzymatic assay of various substances, such as glucose, cholesterol, uric acid, and the like, through the activity of enzymes such as glucose oxidase, cholesterol oxidase, uricase, and the like. The quantity of enzyme substrate present in a sample is determinable from the amount of hydrogen peroxide produced and detected.

Compositions for detecting and/or quantifying hydrogen peroxide in such systems generally comprise a substance having peroxidative activity, such as peroxidase and peroxidase-like substances, and material which undergoes a detectable change, generally a color change, in the presence of hydrogen peroxide and the peroxidative substance. There are many compositions which can be used for such determinations, including mono- and diamines, phenols, polyphenols, aromatic acids, dyes, and other compounds which produce colors under the conditions sought to be detected.

There are many examples of color-forming substrates of peroxidase and peroxidase-like substances which have been previously suggested, including the following substances such as monoamines, diamines, phenols and polyphenols, aromatic acids, dyes including leuco dyes, flavones, epinephrine, gum guaiac, guaiconic acid, water soluble iodides, and bilirubin.

Although the above-named substances are generally useful as indicator systems for the detection of hydrogen peroxide, there are instances in which the concentration of hydrogen peroxide to be analyzed is too low to produce sufficient detectable color from these indicators, e.g., because of the source of the hydrogen peroxide, the necessity for dilution, or the overall detection method. A specific example of such a concentration problem occurs in the detection of hydrogen peroxide produced from the low levels of uric acid present in blood serum (on the order of 1–15 mg/dl). This problem is conventionally ameliorated by measuring relatively large volumes of the detectable product, e.g., by increasing the diameter of the cuvette in a solution assay for uric acid so as to additively increase the relative density of the color produced. However, this solution can only be used when the assay is conducted in a cuvette.

All analytical techniques do not permit the use of such modifications to increase the effective density of the indicator produced. This is a particular problem for use in dry chemistry assay devices, where only a limited amount of color-forming substrate can be incorporated in a strip-type device. In other assays, such as, in solution, the necessity for high dilution levels to obtain proper dissolution or the like, may make it impractical to use increased concentrations of dye.

These problems are particularly acute when the analyte determination is performed in a dry strip assay device such as a multilayer element in which the reagents are impregnated in or coated onto the layers which receive the sample. In these cases, using the relatively thin indicator or reagent layers (on the order of less than one mil) that are desirable in these devices, the density of the color formed can be rather low. Increasing the thickness of the color-forming layer to provide greater density many be undesirable, as it can increase reaction times, create problems in layer preparation, etc. Consequently, other techniques for increasing the effective density of the dye produced in the indicator are necessary, if this type of device is to be used reliably for the assay of low concentration blood serum components. Moreover, in quantitative assays, it may be undesirable to increase the amount of color former beyond a certain level, as this may interfere with the quantitative detection of the analyte.

A number of workers in this field have sought to overcome the problems associated with detection of hydrogen peroxide, and have met with varying degrees of success. Bruschi in U.S. Pat. No. 4,089,747 and Lam, in U.S. Pat. No. 4,119,405, relate to assays for hydrogen peroxide or analytes which generate hydrogen peroxide using a combination of a hydrazone and a color coupler. Use of the hydrazones described in these patents in assaying whole blood has the disadvantage that it is difficult to obtain detectable dyes which absorb electromagnetic radiation at relatively long wavelengths, i.e., greater than about 600 nm. Dyes formed with hydrazones generally absorb at shorter wavelengths and their detection is often hindered by various spectral interferents which are present in whole blood sample. The presence of these interferents, of course, diminishes the accuracy of the assay using dyes formed from hydrazones in testing whole blood.

Evans et al., in U.S. Pat. No. 4,737,457, use a hydrazide, or a hydrazine substituted with at least one electron withdrawing group; these compounds react with phenolic color couplers in the presence of hydrogen peroxide and a peroxidative compound to form a dye which is detectable at a wavelength of 600 nm or greater.

Lam, in U.S. Pat. Nos. 4,071,317; 4,071,318; and 4,071,321, discloses test compositions and devices for detecting peroxidatively active substances. These compositions are based upon the use of borate esters, and are used for dip stick devices which provide a qualitative detection of a pseudo peroxidative substance such as hemoglobin to detect occult blood.

Mast et al., in U.S. Pat. No. 3,986,833, disclose test compositions for detecting peroxidatively active substance including an indicator capable of being oxidized in the presence of a peroxidatively active substance to provide a color change, an oxidizing agent effective to oxidize the indicator, and a potentiating agent. The potentiating agent is a water soluble acid salt or adduct of a quinoline which may be substituted by lower alkyl, hydroxy, thiophenyl, carboxy or lower alkoxy groups.

Washburn, in U.S. Pat. No. 4,672,029, discloses color-forming couplers for combination with an oxidizable color developing compound, such as 4-aminoantipyrine, to provide a chromogenic composition.

Klose et al., in U.S. Pat. No. 4,101,381, describe a dye for photometric detection of hydrogen peroxide. In this case, the dye is formed using as the hydrazone 3-methyl-2-sulfonyl-benzothiazolone-hydrazone. The dye formed by this compound is said to be easily soluble and suitable for use in automatic analyzers, and forms a dye which is measured at 620 or 670 nm. The assay reactions take place in solution, so that the system is not suitable for use in making dry chemistry strips for quick and reliable assays.

Schmitt et al., U.S. Pat. No. 3,770,381, describe dipsticks for semiquantitative colorimetric detection of organic peroxides. The method described therein requires immersing the dipstick in a solution of peroxides in a volatile organic solvent having a boiling point of below 80° C. and withdrawing the dipstick. The dipstick is then placed in a water vapor atmosphere having a relatively constant temperature between about 20° and 100° C. to evaporate the organic solvent and deposit moisture on the surface to produce a color change. This procedure, of course, requires the use of solvent vapor as well as water vapor, and is certainly not convenient to use.

Katsuyama et al., in U.S. Pat. No. 4,418,037, use pyrogallol derivatives to stabilize film used for detecting hydrogen peroxide colorimetrically. The dyes, which must be stabilized, are formed from a hydrogen donor and a coupler.

Yamanisi et al., in U.S. Pat. No. 4,251,629, disclose a composition for colorimetric determination of hydrogen peroxide comprising 4-aminoantipyrine, a N-substituted-3-alkylaniline and a hydrogen peroxide activating agent such as peroxidase. The condensation of the 4-aminoantipyrine with the N-substituted-3-alkylaniline in the presence of hydrogen peroxide produces an indophenol type dye which has a maximum absorption near 545 nm. These dyes are used in solution assays rather than dry chemistry strips.

Babb, in U.S. Pat. No. 4,670,385, discloses triarylmethane leuco dyes which have an aromatic heterocyclic moiety attached to the central methane carbon and which, upon interaction with hydrogen peroxide, provide dyes which absorb at wavelength at least about 600 nm. Because the leuco dyes have limited solubility in water, test compositions or devices using these dyes must be prepared with solvents such as alcohol or N,N- dimethylformamide.

Nix et al., in U.S. Pat. No. 4,247,631, disclose the use of a colored dye based upon the reaction product of a 3-aminobenzoic acid or a 3-aminobenzenesulfonic acid with a 4-aminoantipyrine in the presence of hydrogen peroxide. The dyes formed by this reaction generally have absorption maxima in the range of from about 450–650 nm.

Berti et al., U.S. Pat. No. 4,247,297, disclose indicator dyes useful to test devices comprising a hydrazone and 8-amino-1-naphthol-5,7-diosulfonic acid. Hydrogen peroxide can be quantitatively detected with these compositions using a conventional spectrophotometer at wavelengths ranging from about 490 nm to about 620 run. As with a number of the other assay systems described above, these dyes are not readily usable in a dry reagent strip format.

Bouse et al., U.S Pat. No. 4,971,918, disclose indicator compositions containing a pyrogallol derivative along with a reducible or charge carrier complex forming chromogen. In this case, the indicator system does not require a coupling compound.

Trager et al., in U.S. Pat. No. 4,492,754, disclose a composition for the detection of hydrogen peroxide or hydrogen peroxide forming substrates using a substrate capable of coupling is a compound of the formula:

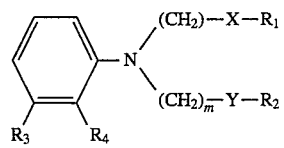

wherein n and m are individually selected from whole numbers 1 to 4,

X and Y, which can be the same or different, represent a valence bond or a phenylene radical, $R_1$ and $R_2$ are individually selected from carboxyl or sulfonic acid groups and one of $R_1$ and $R_2$ can also be hydrogen or lower alkyl, and $R_3$ and $R_4$ are individually selected from hydrogen and alkyl radicals of up to 6 carbon atoms.

These aniline derivatives contain both an acid and a basic group, and are normally present as internal salts or as alkali metal or ammonium salts. Colors formed with these compounds must be read photometrically.

Tsuda et al., in U.S. Pat. No. 4,260,679, disclose reagents for quantitative determination of hydrogen peroxide comprising a hydrogen donor of the formula:

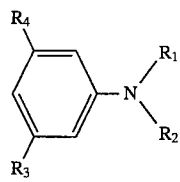

Where $R_1$ is $CH_3$, $C_2H_5$, $CH_2OH$, $CH_2CH_2OH$, $CH_2CH_2NH$.or $COCH_3$;

$R_2$ is $CH_2OH$, $CH_2CH_2OH$, $CH_2CH_2NH_2$, $CH_2NHCOCH_3$, $CH_2CH_2NHCOCH_3$, or $COCH_3$;

$R_3$ is H, $CH_3$, $C_2H_5$ or $OCH_3$; and $R_4$ is H or $CH_3$.

Electron acceptors used with these compounds are conventional materials such as 4-aminoantipyrine, 2-thio- phenecarboxylic acid hydrazide, benzidine or 3-methyl -2- benzthiazolinione hydrazone.

No admission is made that any reference cited herein constitutes prior art, and applicants reserve the right to challenge the nominal publication date or alleged teachings of any cited reference.

SUMMARY OF THE INVENTION

Coupling compounds are provided which react with hydrazones or 4-substituted amino antipyrines to form intense colors in the presence of hydrogen peroxide. These N,N-disubstituted anilines have the structure shown in FIG. 1, where $R^1$ and/or $R^2$=H, $C_1$–$C_9$ alkyl, $C_1$–$C_9$ alkoxy, $NR^3R^4$ (where $R^3$ and/or $R^4$=H, $C_1$–$C_9$ alkyl, aryl, or heteroaryl), F, Cl, Br, I, $COOR^5$ (where $R^5$= H, $C_1$–$C_9$ alkyl, aryl, or heteroaryl), CN, $CONR^6R^7$ (where $R^6$ and/or $R^7$= H, $C_1$–$C_9$ alkyl, aryl, or heteroaryl), aryl, aryloxy, heteroaryl, heteroaryloxy; and $R^{11}$, $R^{12}$, $R^{13}$, and/or $R^{14}$= H, $C_1$–$C_9$ alkyl, $C_1$–$C_9$ alkoxy, $NR^{15}R^{16}$ (where $R^{15}$ and/or $R^{16}$= H, $C_1$–$C_9$ alkyl, aryl, or heteroaryl), F, Cl, Br, I, $COOR^{17}$ (where $R^{17}$= H, $C_1$–$C_9$ alkyl, aryl, or heteroaryl), CN, $CONR^{18}R^{19}$ (where $R^{18}$ and/or $R^{19}$= H, $C_1$–$C_9$ alkyl, aryl, or heteroaryl), aryl, aryloxy, heteroaryl, heteroaryloxy or any other group that does not interfere with the coupling reaction; and n=0–10 and m=0–10 and Z and/or Y=H, OH, SH, $COOR^8$ (where $R^8$=H, $C_1$–$C_9$ alkyl, aryl, or heteroaryl), CN, $NR^9R^{10}$ (where $R^9$ and/or $R^{10}$= H, $C_1$–$C_9$ alkyl, aryl, or heteroaryl), $NR^{20}NHR^{21}$ (where $R^{20}$ and/or $R^{21}$= H, $C_1$–$C_9$ alkyl, aryl, or heteroaryl), where at least one of Z or Y is $COOR^8$, CN $NR^9R^{10}$, or $NR^{20}NHR^{21}$.

The term "aryl" includes substituted and unsubstituted single, plural and fused ring groups which have aromatic bonding, including but not limited to phenyl, naphthyl, biphenyl, fluoryl, pyryl, and the like. Substituents on the aryl ring may be any substituents which do not interfere with coupling to the desired hydrazone or aminoantipyrine, including but not limited to $C_1$–$C_5$ alkyl, $C_1$–$C_5$ alkenyl, F, Cl, Br, I, hydroxyl, $C_1$–$C_5$ alkoxy, CN, $COOR^1$, $CONR^6R^7$, and any combination thereof. Likewise, the alkenyl and alkyl groups may be substituted by F, Cl, Br, I, hydroxyl, CN, and other groups which do not interfere with the coupling.

The term "heteroaryl" encompasses rings having aromatic bonds having at least one heteroatom in the ring. The heteroatoms may be N, S or O, and any combination thereof. Examples of the heteroaryl groups which can be included in the diamines of the present invention include pyridine, quinoline, isoquinoline, pyrazine, pyrimidine, purine, oxathialone, oxazole, dithiazine, indole, xanthene, acridine and the like. These heteroaryl groups may likewise be substituted at one or more positions by at least one substituent selected from the group consisting of $C_1$–$C_5$ alkyl, $C_1$–$C_5$ alkenyl, $C_1$–$C_5$ alkoxy, CN, $COOR_1$, $CONR_6R_7$, and the like.

Additionally, methods are provided for synthesizing the aniline derivatives of the present invention.

The appended claims are hereby incorporated by reference as a further description of the preferred embodiments.

BRIEF DESCRIPTION OF THE DRAWINGS

FIG. 2, formula 2, shows a formula for dyes according to the present invention.

FIG. 5 illustrates some coupling compounds that can be used to form dyes according to the present invention.

DETAILED DESCRIPTION OF THE PREFERRED EMBODIMENTS

The N,N-disubstituted aniline, in the presence of a catalyst such as hydrogen peroxide, react with a hydrazone or aminoantipyrine para- to the anilino group to form a darkly colored compound. These dyes thus are useful in detecting compounds which form hydrogen peroxide, particularly those that form hydrogen peroxide as a result of the action of an enzyme, such as glucose in the presence of glucose peroxidase, or cholesterol in the presence of cholesterol oxidase. In the dyes formed from these coupling compounds, the immobilizable functional group is part of the chromophoric moiety, so that the dyes can readily be immobilized onto solid support matrices. Additionally, these dyes are highly resistant to interfering reducing substances such as ascorbic acid.

Figure 1:
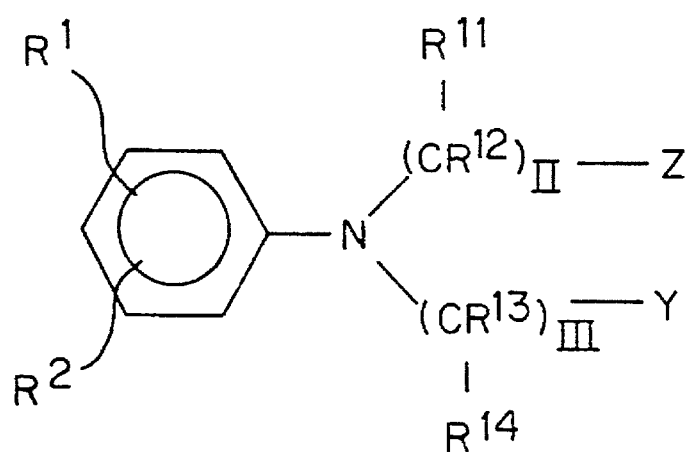
FIG. 1 shows coupling compounds which react with hydrazones or 4-substituted amino antipyrines to form intense colors in the presence of hydrogen peroxide.
Figure 2:
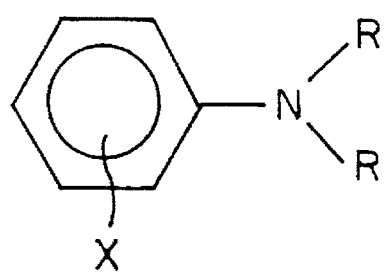
FIG. 2, formula 1, shows a formula for commercially available dyes.
Figure 2:
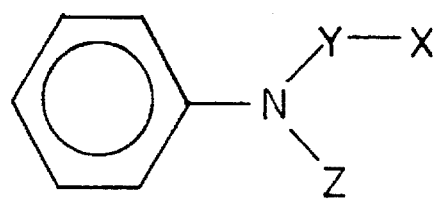

Commercially available dyes, as described in formula (1) in FIG. 2, contain the immobilizable functional group X that is attached to, but not part of, the chromophore; consequently, its identity and configuration do not affect the molar absorptivity of the dye, its maximum wavelength, or the intensity of absorbance at a particular desired pH.

The dyes made according to the present invention, however, as shown in formula (2) in FIG. 2, contain the immobilizable functional group X as part of the chromophore. The functional group X is attached via group Y, Z or a combination of Y and Z, to the chromophoric moiety of the dye. Because the functional group X is coincident with the chromophoric moiety of the dye, the nature of the functional group X and its mode of attachment Y directly affect the molar absorptivity of the dye, its maximum wavelength, and the intensity of absorbance at a particular desired pH. Using the coupler-hydrazone combination of the present invention, one can readily custom design new dyes to fit the requirements of the analytical method of interest.

Figure 3:
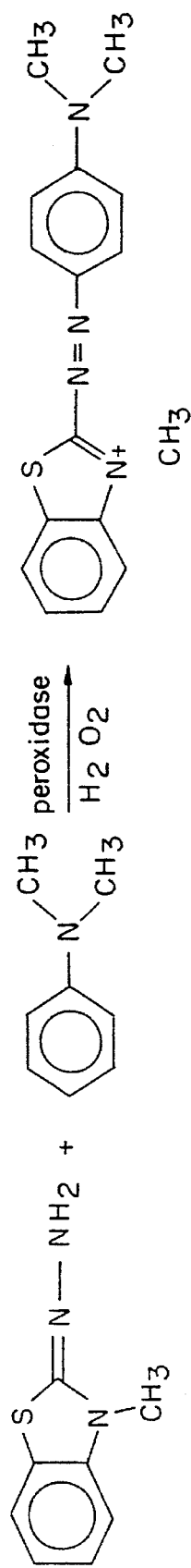
FIG. 3 shows a possible mechanism for the coupling of dye components according to the present invention.

The reaction of two colorless or lightly colored dye components, such as a hydrazone or an aminoantipyrine and an N,N-disubstituted aniline, in the presence of a catalyst such as peroxidase and hydrogen peroxidase, produces an intensely colored compound. The coupling of the dye components is believed to occur through the mechanism shown in FIG. 3. However, in this illustration, the coupling of the aniline derivative and the hydrazone or aminoantipyrine does not involve the portion of the molecule where coupling to the substrate occurs.

The dyes formed by the process of the present invention have functional groups on the aniline amino moiety, such as amino or carboxylate, which anchor the dye to solid substrates. Since these dyes are anchored to the substrates, they do not intimately mix with other reagents in an analytical system until the sample stream contacts the dyes. Therefore, these dyes are more stable and produce more intense color in analyses than do conventional dyes. Moreover, the dyes of the present invention are highly resistant to inference from ascorbic acid that may be present in the system.

Among the hydrazones that can be used in the present invention are those which are condensation products of a hydrazine with an aldehyde or ketone and contain the grouping >C=NNH$_2$. Many hydrazones are capable of coupling with anilines to form a colored entity. Among these hydrazones are 3-methyl-2-benzothiazolinone hydrazone, 1-methyl-2-quinoline hydrazone, N-methyl-pyridone-4-hydrazone, N-methyl-pyridone-2-hydrazone, N-methyl-quinoline-2-hydrazone, N-methyl-quinoline-4-hydrazone, N-methyl-2-benzothiazolinone hydrazone, N-methylthiazolinone-2-hydrazone, N-methyl-4-phenylthiazolinone-2-hydrazone, N-methyl-oxazolinone-2-hydrazone, N-methyl-benzoxazolinone-2-hydrazone, 1,3-dimethyl-2-benzimidazolinone-2-hydrazone, and 3-($C_1$–$C_4$-alkyl)-2-benzothazolinone hydrazones such as 3-methyl-2-benzothiazolinone hydrazone (MBTH). These hydrazones are all strong reducing agents.

Dyes can also be formed with 4-substituted antipyrines to give color in the presence of hydrogen peroxide. Among these compounds are 4-aminoantipyrine, 4-(dimethylamino)antipyrine, 4-(ethylaminoantipyrine), 4-(methylamino)antipyrine, 4-(sodium sulfonatomethylamino)antipyrine, 4-(sodiumsulfonatomethyl) (isobutyl)aminoantipyrine, 4-(sodium sulfonatomethyl) (methyl) amino antipyrine, and 4-(isopropyl)antipyrine.

The acid addition salts of the hydrazones or the aminoantipyrines can also be used. Any conventional acid addition salt can be used, such as those formed from hydrochloric acid, hydrobromic acid, sulfuric acid, nitric acid and the like. These acid addition salts can either be used alone or in conjunction with the corresponding hydrazone.

Figure 4C:
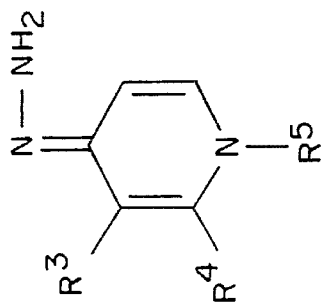
FIG. 4C illustrates 4-pyridyl hydrazones which can couple to aniline derivatives of the present invention to form dyes.
Figure 4B:
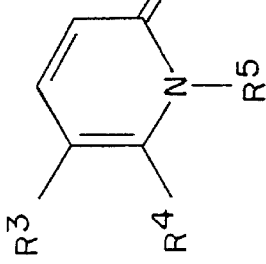
FIG. 4B illustrates 2-pyridyl hydrazones which can couple aniline derivatives of the present invention to form dyes.
Figure 4A:
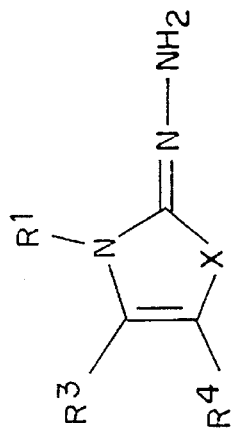
FIG. 4A illustrates oxazole hydrazones which can couple to aniline derivatives of the present invention to form dyes.

More general formulas for the hydrazones which can be coupled to aniline derivatives as described above to form the dyes of the present invention are shown in FIG. 4, in which $R^1=C_1-C_4$ alkyl, X=S, O, or $NR^2$, where $R^2=C_1-C_4$ alkyl. $R^1$ and $R^2$ may be the same or different. The heteroatom X at this position must be saturated. $R^3$, $R^4$=phenyl, pyridinyl, naphthyl, or quinolidyl, and may be the same or different or $R^3+R^4$=a fused benzene, pyridine, naphthalene, or quinoline ring. The saturated ring nitrogen must be at a position vicinal to the hydrazone functional group, as shown in FIG. 5, where $R^5=C_1-C_4$ alkyl. $R^3$, $R^4$= phenyl, pyridinyl, naphthyl, or quinolidyl, and may be the same or different or $R^3+R^4$= a fused benzene, pyridine, naphthalene, or quinoline ring. The saturated ring nitrogen must be at a position ortho or para to the hydrazone functional group.

Among the coupling compounds that can be used to form dyes according to the present invention are the following:

N, N-(biscarboxymethyl) aniline (PAGA)

N, N-(biscarboxymethyl) -4-methoxyaniline (MOPAGA)

N, N-(bis-β-carboxyethyl)aniline (PAPA)

N-ethyl-N-phenylglycine (EPG)

N-ethyl-N-carboxyethylaniline (NENCEA)

N-phenylpiperidinyl succinate (PPS)

N-ethylanilinopropaneamine (NEAP)

N-methylanilinopropaneamine (NMAP)

N-methyl-N-carboxyethylaniline (NMNCEA)

N,N- (bis-β-carboxyethyl)-2,5-dimethylaniline (BCEDMA)

N-β-carboxyethylaminobenzoic acid (NCEABA)

The molar ratios of hydrazone/coupler range from about 20:1 to about 1:20 with more nearly equimolar ratios being preferred for the optimum combination of detection sensitivity and interference resistance.

Test means prepared with the dye formulations of the present invention, and test systems employing these test means, are preferably used in a generally neutral or slightly acid pH range, although the dyes remain operative even at a somewhat higher pH. The maintenance of a generally neutral or acid pH provides improved reactivity in terms of speed and resistance to interference.

The dyes formed according to the present invention are extremely stable because the functional groups are on the aniline moiety. Therefore, there is no need for stabilizing agents. Additionally, the dyes formed are substantially more resistant to ascorbic acid interference, particularly at ascorbic acid levels above 10 or 20 mg/dL sample, than is the conventional dye dimethylaniline (DMA). Preferably, the percent recovery is at least 85%, more preferably at least 90%.

The coupling compounds react with the N,N-disubstituted aniline compounds in the presence of hydrogen peroxide.

Many analytes, including glucose, cholesterol, uric acid, etc. produce hydrogen peroxide when acted upon by a peroxidase enzyme, an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase). Peroxidase also occurs in microorganisms and may be produced by fermentation. Certain synthetic peroxidases, such as those disclosed by Theorell and Maehly in *Acta. Chem. Scand.*, Vol. 4, pages 422–434 (1950), are also satisfactory for uses in hydrogen peroxide detection systems. Less satisfactory are substances such as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes, but which demonstrate peroxidative activity and could be used as oxidizers, are iron sulfocyanate, iron tannate, ferrous ferrocyanide, chromic salts (such as potassium chromic sulfate) absorbed in silica gel, etc.

Among the analytes that can be determined by determining hydrogen peroxide produced by action of an oxidizing agent on the analyte are glucose, cholesterol, uric acid, choline esterase, phospholipids, creatine or creatinine. All of these assays can readily be conducted using the dye formed according to the present invention.

An optional buffer may be included in the reagent or dye-forming composition, thereby increasing the range of compounds which can be successfully used for color-forming. These optional buffers establish the pH of the reaction medium at a level which is conducive to the formation of a dye while not inhibiting the dye-forming reaction. Useful buffers include carbonate buffers such as sodium and potassium carbonate, borate buffers such as sodium and potassium borate, citrate, phosphate and glutarate buffers and the trismaterials such as tris(hydroxymethyl)aminomethane. Some of these materials buffer the reagent composition to a range of between about 5.0 and 10.0 which is a useful pH range for detecting, for example, blood serum components using the dye-forming components described herein.

In the specification, the term "reagent layer" is used to refer to a layer in which an analyte is converted into a visually detectable species in the presence of the dye composition of the invention. This basically comprises a substance having peroxidase activity and a substance capable of causing a detectable change in the presence of hydrogen peroxide and the substance having peroxidase activity. In this case, the substance capable of causing a detectable change in the presence of hydrogen peroxide and the substance having peroxidase activity is the combination of the N,N-disubstituted aniline and the coupling compound of the present invention.

In use, the reagent, i.e., the substance which reacts with the analyte of interest to form hydrogen peroxide, can be incorporated in an assay device with the dye-forming substance, or can be in a layer separate from the dye-forming substance. The formation of a colored dye with the N,N-disubstituted aniline and the coupler indicates the presence and/or concentration of a desired analyte, or a reaction or decomposition product of the analyte.

The term "substance having peroxidase activity" is used to mean a substance which catalyzes oxidation of a hydrogen donor with hydrogen peroxide (as a substrate) and is well recognized in the art. Examples of substances having peroxidase activity include peroxidase extracted from various organisms, synthetic peroxidase and other chemical substances extracted from organisms which exhibit an activity similar to peroxidase. Of these, horseradish peroxidase is preferred.

In a test device, a color-forming reaction layer can contain an analyte component which differs from hydrogen peroxide, which is hereinafter referred to an "analyte precursor component", and a reagent composition system capable of forming hydrogen peroxide through chemical reaction. Alternatively, a reagent layer containing the reagent system for forming hydrogen peroxide can also be provided separately from the reagent layer or any other layer in the test device.

The hydrogen peroxide forming reagent layer can be any reagent composition system in which hydrogen peroxide is produced from the analyte precursor component through chemical reaction in one step or a reagent composition system in which hydrogen peroxide is produced from the analyte precursor component through chemical reaction comprising continuous enzyme reactions. One example of such reaction is, for example:

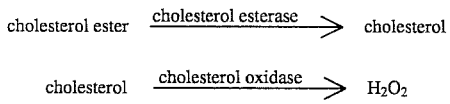

in a plurality of steps. Depending upon the hydrogen peroxide-forming reagent system, the reagent system for forming hydrogen peroxide can be incorporated into the reagent layer, the color-forming reaction layer or the dye-fixing layer, or a single layer or a plurality of layers different from the aforesaid layer can be provided as the hydrogen peroxide-forming layer.

The dye-forming formulation of the present invention can be incorporated in a dry analytical element such as a multilayer assay device, which generally comprises an absorbent carrier material, i.e., a self-supporting absorbent sheet or pressed material, such as filter paper or strips, which contains the analytical composition and optionally, any other desired reagents such as the peroxidative substance.

When used in a dry multilayer assay device, the dye-forming composition can be incorporated into a suitable carrier material by imbibition, impregnation, coating, or by immobilization onto an insoluble matrix. Useful carrier materials are those which are insoluble and maintain their structure integrity when exposed to water or physiological fluids such as urine or serum. Useful elements can be prepared from paper, porous particulate structure, cellulose, wood, glass fibers, woven and nonwoven fabrics (both synthetic and nonsynthetic) and the like. A useful dry analytical device is made by imbibing a solution of the analytical composition into the material and drying.

The components of the analytical composition, as well as the peroxidative substance, interactive component, etc., can be incorporated in any of the element zones. The location of individual components is well within the skill of a worker in the clinical chemistry art.

Because the dyes formed according to the present invention include an immobilizing group, they are particularly well suited for dry chemistry assay devices. The immobilizing group enables these dyes to be used for quantitative as well as qualitative assay devices.

One example of a self-contained analyzer that quantitatively detects an analyte in a biological fluid is disclosed in Ertingshausen, U.S. Pat. No. 5,087,556, the entire contents of which are hereby incorporated by reference. This exemplary device includes a channel that is connected to a first compartment or open reservoir. The biological fluid sample that is deposited into the first open reservoir is drawn into the channel by capillary and/or wicking action. The drawing of the biological fluid into the channel can be assisted by wicking in the channel.

The channel of the device of this invention contains or encloses at least one reagent for detecting the presence of a selected analyte in the biological fluid. The reagent used in this invention can be a combination of compounds and/or enzymes that react simultaneously or sequentially with the selected analyte to produce a detectable reaction product. Desirably, the detectable reaction product produces a color change that is visible to the naked eye. These reagents must be immobilized either on the wall of the channel or in a material that is, desirably, stationary within the channel. When more than one reagent is required to detect an analyte, the reagents are, desirably, immobilized in their reaction sequence within the channel or within the first open reservoir and the channel. The reagent that produces the detectable reaction product must be present in a calibrated or predetermined concentration within the channel.

In one embodiment of a device onto which a dye of the present invention may be immobilized for quantitative analysis, a material is located within the measurement channel which can receive an immobilize thereon the compounds forming a dye according to the present invention. Suitable materials are natural or synthetic membranes, which are chemically compatible with the components of the dye. Suitable membranes are commercially available and can be porous or fibrous materials including filter paper or nylon cloth. The membrane is desirably an integral part of the channel, such as the bottom of the channel, and is sealed in place.

Because the dye-forming components are immobilized in the measurement channel, as fluid sample moves through the assay device, it will not pull the dye components along with it through the measurement channel. This, of course, is essential when conducting quantitative analyses, as the quantity of sample is generally read by measuring the extent to which a color change has moved through the measurement channel and correlating it with a standard or measurement scale to relate to the amount of analyte present in the sample.

The amount of the dye-forming components can be varied widely. Generally, the hydrazone or aminoantipyrine coupling compound is present in a coverage of at least about 100, and preferably from about 300 to about 5000 mg/m$^2$. The N,N-disubstituted aniline compound is generally present in coverage of at least about 100, and preferably from about 1000 to about 5000 mg/m$^2$. The peroxidative substance can be present in a coverage generally of at least about 25,000, and preferably from about 50,000 to about 100,000 I.U./m$^2$ for peroxidase. A variety of other desirable but optional reagents and additives can be present in the element in amounts known to one skilled in the art. Such materials include surfactants, buffers, binders, pigments, activators, reagents or interactive compositions, etc.

Many different types of elements, depending upon the method of assay, can be prepared in accordance with the present invention. Assay devices can be configured in a variety of forms, including elongated tapes of any desired width, including elongated tapes of any desired width, sheets, slides or chips.

Assays conducted with the color-forming dyes of the present invention can be manual or automated. In general, in using a multilayer assay device, hydrogen peroxide or analyte determination is made by physically contacting the device with a sample, of approximately 1–2000 μl, of the liquid to be tested such that the sample mixes with the reagents within the element. This contact can be accomplished by dipping or immersing the element into the sample. Alternatively, particularly for a quantitative assay, a controlled amount of sample is dropped onto a sample initiation area of a device. In another embodiment of the invention, a sample well is provided prior to the sample initiation area to ensure that the correct amount of sample to provide a reliable result is added to the device.

Determination of hydrogen peroxide or an analyte is achieved when the coupler and the N,N-disubstituted aniline compound react to form a dye. This dye can be detected with the unaided eye or with suitable spectrophotometric means and procedures at a wavelength greater than or equal to 600 mn. Generally, the dyes formed in the practice of this invention have an absorption maximum equal to or greater than 600 nm. Because of their intense color, they are more suited for use in dry assays without the need for instrumentation.

The dye-forming compositions of the present invention can be used in both solution and dry element assays. In a solution assay, generally the N,N-disubstituted aniline, the hydrazone or 4-aminoantipyrine, and peroxidative substance are physically contacted and mixed with a liquid test sample in a suitable container, such as a test tube, Petri dish, beaker, cuvette, or the like. The resulting solution is incubated for a relatively short time, about less than five minutes, at a temperature of up to about 25° C. The sample is then evaluated by measuring the amount of dye provided upon interaction with hydrogen peroxide. The amount of dye can then be correlated to the amount of hydrogen peroxide either initially present in the sample, or produced as a result of the presence of an analyte. The evaluation can be effected visually or with suitable colorimetric detection equipment and procedures.

Alternatively, the composition and method of the present invention can be used with a dry analytical element which can be a simple carrier matrix, such as a thin sheet of self-supporting absorbent or bibulous materials, such as filter paper or strips, which contain the dye composition with or without the peroxidative substance. Preferably, these elements also contain the peroxidative substance. These elements are known in the art as test strips, diagnostic elements, dip sticks, diagnostic agents and the like.

When employed in "dry chemistry" elements, the dye composition of the present invention can be incorporated into a suitable carrier matrix by imbibition, impregnation, coating or other suitable technique. Useful carrier matrices are insoluble and maintain their structural integrity when exposed to water or physiological fluids such as urine or serum. The dye components of the present invention, as well as the peroxidative substances, can be incorporated in any of the zones of the elements that would be suitable for the particular analysis. The location of individual components is within the skill of a worker in the clinical chemistry art.

Assays for analytes using the dye composition of the present invention can be manual or automated. In general, using the dry elements, hydrogen peroxide or analyte determination is made by taking the element from a supply roll, chip packet or other source and physically contacting it with a sample of the liquid to be tested. This contact can be accomplished in any suitable manner, including dipping or immersing the element into the sample or, preferably, spotting the element by hand or machine with a drop of the sample with a suitable dispensing means. After sample application, the element is left for a period of generally less than five minutes while any hydrogen peroxide formed from the analyte in the sample causes the N,N- disubstituted phenylaniline to couple with the hydrazone or 4-aminoantipyrine to form a dye. This dye can be detected with the unaided eye or with suitable spectrophotometric means and procedures. Alternatively, for a quantitative assay, the element can be designed so that a color bar is formed which is proportional to the amount of hydrogen peroxide in the sample or formed by the analyte in the sample with the peroxidative agent.

The dye-forming components of the present composition can be packaged in kit form along with or separate from the peroxidative agent. The individual components are packaged in amounts sufficient to conduct one or more assays when mixed together in a suitable container with water or other liquid medium.

The N, N-disubstituted anilines of the present invention can be prepared by reacting the corresponding amine with an alkali metal hydroxide to hydrolyze the amine. The hydrochloride salt is formed by treatment with hydrochloric acid. Alternatively, the N, N-disubstituted anilines are prepared from aniline. In addition, the compounds can be prepared on a large scale by a procedure according to the present invention.

The following examples are given for purposes of illustration only, and are not meant to be limiting of the scope of the invention.

EXAMPLE 1

Preparation of N-ethyl-N-carboxyethylaniline hydrochloride (NENCEA.HCl)

51.7 grams of 3-(N-ethyl-N-phenyl)-aminopropanamine was combined with 500 mL of 3M sodium hydroxide in a one liter round-bottom flask and refluxed for 3.25 hours, until the solution was clear and homogeneous. The solution was then cooled to room temperature. A strong smell of ammonia confirmed the hydrolysis of the nitrile to the carboxylic acid.

The solution was neutralized with 150 mL 18° Bé muriatic acid (approximately 28% hydrochloric acid) and extracted three times with 100 mL diethyl ether. The ether extracts were combined and washed twice with 100 mL water, once with 100 mL saturated sodium bicarbonate solution, once with 100 mL water, and once with 100 mL saturated brine.

The original reaction mixture was reacidified to pH 6 and the extraction and washing process were repeated. All of the washed ether fractions were combined and reduced in vacuo to 48 grams of a green-brown viscous fluid.

The hydrochloride salt was obtained by dissolving the crude free acid-free base obtained above in 100 mL 12% HCl and refluxing gently for ten minutes. The water was distilled off, and the remainder was transferred to a beaker. Then, 250 mL of benzene was added in portions while boiling to azeotrope off the remaining water. Crystals formed as the water was removed. The crude product was recrystallized from ethanol. Ten grams of snow white crystals were collected.

EXAMPLE 2

Large Scale Preparation of N-ethyl-N-carboxyethylaniline hydrochloride (NENCEA.HCl)

Into a five liter reaction vessel fitted with a heating jacket, reflux condenser, temperature controller and mechanical stirrer were placed 1700 g (9.77 mol) N-ethyl-N-cyanoethylaniline and 33% water solution of 860 g (15.36 mol) KOH. The reactants were stirred and the heterogeneous mixture was heated for six hours at 105°–110° C. During the heating the nitrile was hydrolyzed, as evidenced by the strong smell of ammonia produced thereby. The ammonia was removed from the effluent by bubbling the ammonia into sodium bicarbonate. After six hour of stirring, a homogeneous solution was obtained, which was cooled to room temperature and acidified with 3480 g of concentrated (12N) hydrochloric acid. The acidified solution was cooled to 20° C., whereupon N-ethyl-N-carboxyethylaniline hydrochloride precipitated out of solution. The product was collected in a Büchner funnel and the filter cake was rinsed twice with three liters of acetone. The yield of dry product was 1670 g, 71.5%.

EXAMPLE 3

Preparation of N,N-bis-(carboxymethyl)aniline (PAGA)

This compound was prepared from 14.6 mL (0.16 mol) aniline, 100 mL 1.6M n-butyl lithium in hexane, and 76.3 g (0.65 mol) sodium chloroacetate. The reactants were mixed together and the reaction was conducted in a 500- mL, three neck RB flask which was oven dried and cooled in a desiccator, and equipped with a condenser and Claisen adapter, mechanical stirrer, nitrogen bubbler, septum. The flask was flushed with nitrogen, and 14.6 mL aniline was charged to the flask, to which 200 mL freshly distilled THF was added. The solution was cooled to 0° C. in an ice bath.

A freshly opened 100- mL bottle of 1.6M n-butyl lithium in hexane was cannulated into the cooled solution over a period of ten minutes, and the solution was stirred at 0° C. for one hour. The reaction was then brought to room temperature and stirred at room temperature for one additional hour.

Then, 76.3 grams sodium chloroacetate was added via powder funnel under a stream of nitrogen. The slurry was stirred mechanically, and set to reflux for 24 hours.

The THF/hexane solvent was evaporated with mild heat and mechanical stirring until only a solid remained. Then, 200 mL water was added to dissolve the salts, and the entire mixture was transferred to a separatory funnel. The mixture was extracted three times with 100 mL dichloromethane, and the aqueous phase was reserved.

The aqueous layer was acidified with about 40 mL concentrated HCl to pH approximately 1, at which point an oil formed. The solution was set in a 0° C. freezer overnight. The crystals formed were collected and washed with water. The product was recrystallized from ethanol to give 6.2 grams of colorless, flocculent material, in 19% yield.

EXAMPLE 4

Preparation of N,N,bis-(Carboxymethyl)-4-methoxyaniline (MOPAGA)

N,N,bis-(Carboxymethyl)-4-methoxyaniline (MOPAGA), the 4-methoxy analog of PAGA, was prepared as in Example 3 from 16 mmol of p-anisidine, 16 mmol n-butyllithium and 65 mmol sodium chloroacetate.

To recover the MOPAGA, the THF/hexane solvent was evaporated and the residue was dissolved in 25 mL water and extracted four times with 30 mL ether. Four mL of concentrated HCl was added until the solution became cloudy. The solution was cooled, at which point a precipitate formed. The precipitate was collected and recrystallized from water to give beige needles. The yield was 1.3 grams, or about 34%.

EXAMPLE 5

Preparation of N-ethylanilinopropaneamine (NEAP)

In a stainless steel pressure reactor, 400 grams (2.44 mol) of N-ethyl-N-cyanoethyl aniline was placed with 800 mL methanol and 30 g Raney nickel. The reactor was fitted with a cooling jacket. The mixture was hydrogenated with stirring at 70° C. and at 60 atm pressure until the hydrogen pressure ceased falling. This took about four hours; when the hydrogen pressure ceased falling, hydrogen was no longer being consumed. The methanol was evaporated in vacuo with a 300 mm rectification column. The fraction distilling at 100°–120° C./2 mm. It was distilled a second time from solid NaOH, and the fraction distilling at 120°–125° C./2 mm was collected. The yield was 60%. Two hundred grams (1.19 mol) of N-ethyl-N-(3-aminopropyl)aniline was dissolved in one liter of 2-propanol, and dry HCl was passed through the acidity the solution and form the hydrochloride salt. After cooling to 10° C. for two hours, the crystalline product was collected in a Büchner funnel and washed with 2-propanol and diethyl ether. The washed product was dried in vacuo at 50° C. The yield of the dry product was 90%, mp 20°–202° C.

EXAMPLE 6

Synthetic Methods for Analogs

In this method, compounds of the following formula were produced:

For compound 6, $R_1$=$CH_2CH_2COOH$; $R_2$=$R_3$=$CH_3$

For compound 7, $R_1$=$CH_3$, $R_2$=$R_3$=H

For compound 8, $R_1$=$R_3$=H; $R_2$=COOH

To prepare the above compounds, 0.05 g hydroquinone was added to a solution of 35 mmole aniline in 12.5 mL acetic acid. The mixture was cooled to 10°–12° C., and 5 mL (74 mmol) acrylic acid was added. The mixture was stirred an additional hour, after which it was warmed to 60° C. and stirred for six hours at the elevated temperature. The acetic acid was evaporated off under reduced pressure and 10 mL hot butanol added to the residue. Upon cooling, crystals formed which were collected and recrystallized from an appropriate solvent.

The hydrochloride salts were formed by dissolving the crude material in concentrated HCl, evaporating water formed, and recrystallizing the product from ethanol.

2, 5-dimethyl-N,N-(β-carboxyethyl) aniline monohydrate (compound 6)

Yield: 35%; mp 85°–87° C. (hexane) calculated and found atomic masses are shown in Table 1.

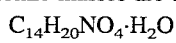

TABLE 1

|  | C | H | N |
|---|---|---|---|
| calcd | 59.4 | 4.9 | 8.0 |
| found | 59.6 | 5.0 | 8.0 |

N-(β-carboxyethyl)-N-methylaniline hydrochloride (compound

Yield: 30%; mp 137°–138° C. (dioxane) calculated and found atomic masses are shown in Table 2.

$C_{10}H_{13}NO_2 \cdot HCl$

TABLE 2

|  | C | H | N |
|---|---|---|---|
| calcd | 55.7 | 7.3 | 6.5 |
| found | 55.7 | 6.9 | 6.5 |

2-β-carboxyethylaminobenzioc acid (compound 8)

Yield: 33%; mp 184°–185° C. (methanol) calculated and found atomic masses are shown in Table 3.

$C_{10}H_{11}NO_4$

TABLE 3

|  | C | H | N |
|---|---|---|---|
| calcd | 57.4 | 5.3 | 6.7 |
| found | 57.1 | 5.4 | 6.6 |

EXAMPLE 7

Immobilization of a Dye onto a Functionalized Insoluble Matrix

PAPA, N,N'-bis(β-carboxyethyl)aniline, was immobilized onto aminopropyl-functionalized silica (ap-DS710). This functionalized silica was prepared by slurrying together 150 Davisil 710 silica and 600 grams of a 5% w/w γ-aminopropyltriethoxysilane solution in acetone and refluxing for 16 hours. This silica was collected, washed with acetone, dried for 24 hours, and then stored in a low-humidity atmosphere.

Four grams of N,N'-bis(β-carboxyethyl)aniline was slurried in 60 mL $CHCl_3$. Then, 7.1 mL thionyl chloride and ten drops DMF were added and the mixture was warmed gently (just below reflux) for one hour, until the solution was clear and light brown in color. The reaction mixture was cooled to room temperature and evaporated in vacuo to a viscous dark syrup.

In an appropriately sized Erleneyer flask, ten grams of ap-DS710 silica was slurried with triethylamine and 20 mL methylenetrichloride in an ice bath. The acid chloride syrup produced above was dissolved in 10 mL methylenetrichloride and added by pipet to the slurry. The flask was stoppered and the reaction mixture was stirred at 0° C. for 30 minutes, then at ambient temperature for one hour. The product was collected in a Buchner funnel, and the filter cake was washed with 100 mL each of methylenetrichloride, acetone, water, 0.5M sodium bicarbonate solution, and finally with water. The product was removed to a shallow dish and dried for at least 16 hours in a low humidity atmosphere (5% or less relative humidity).

EXAMPLE 8

Device for Quantitatively Detecting Hydrogen Peroxide

Preparation of Analytical Film

A 12"×5" swatch of polyester fabric (PeCap® from Tetko, Briarcliffe Manor, N.Y.) was attached to a glass plate using double-stick tape. A paste containing 0.25 gram of the dyed matrix as prepared above, 125 µL of 20 mg MBTH.HCl in methanol, 100 µL of 18 mg/1.5 mL water, 200 µL of anhydrous methanol and 400 µL of polyvinylacetate, medium MW, 12% methanolic solution, a film-forming polymer was placed at one end of the swatch, and a film was drawn down onto the fabric using a film-casting knife (Paul N. Gardner Company, Pompano Beach, Fla.) set at 1 mil (0.001 inch). The film was dried at 40° C. for ten minutes, and then 5 mm wide strips were cut and heat sealed with polyester top and bottom films to form very precise flow channel.

Determination of Hydrogen Peroxide

Plasma with varying concentrations of hydrogen peroxide was introduced into the channels prepared above. As the samples flowed through the channels, dark blue color bars formed with sharp color fronts. The length of the color bars was proportional to the concentrations of hydrogen peroxide in each sample. Representative data are shown in the following table:

TABLE 4

| Color Bar Length vs. Hydrogen Peroxide Concentration | |
|---|---|
| [$H_2O_2$] | Bar Length |
| 2 mM | 1.9 cm |
| 4 mM | 3.2 cm |
| 8 mM | 6.0 cm |

The coupled dyes of the present invention can be used in test means which take many physical forms and include many specific compounds for coupling with the hydrazones. These, along with reagents which can additionally be employed, if desired, are described. Testing means prepared with these compounds can be used in both liquid and solid form.

Although the above examples show test devices for use in quantitative analysis, the dye formulations of the present invention can also be used in qualitative test devices. For example, the hydrazone and aniline derivatives can be impregnated on a filter paper or other absorbent sheet which is also impregnated with glucose oxidase or other enzyme which forms hydrogen peroxide in the presence of a desired analyte. The presence of a substrate for the enzyme on the test device forms a dark color on the test strip.

The dyes of the present invention are remarkably resistant to ascorbic acid interference. This is particularly useful in primary assays that are used over a period to time, such as for patients who must periodically monitor their cholesterol or glucose levels. Since many of these patents take vitamin C (ascorbic acid) supplements, when using assay devices prepared using the dyes of the present invention, they need not abstain from vitamin C supplementation prior to checking their cholesterol or glucose levels.

For persons who supplement their diets with ascorbic acid, the level of ascorbic acid in a blood sample is generally in the range of about 10 mg/dL. Many conventional dyes for determination of hydrogen peroxide do not give accurate readings in the presence of ascorbic acid. The dyes formed by the coupling combination of the present invention were tested for resistance to the presence of ascorbic acid by adding ascorbic acid in varying quantities to a liquid which was then added to dyes formed according to the present invention. The absorptivity of the dye in the absence of ascorbic acid was 100, and the absorptivity of the dye in the presence of varying quantities of ascorbic acid was expressed as a percentage of the original absorbance.

Table 2 shows the result of the above experiment for DMA, a commercially available dye, as well as five of the dyes prepared according to the present invention. It can be seen from Table 2 that the dyes of the present invention are much more resistant to ascorbic acid in ranges above about 10 mg ascorbic acid/dL of sample than is the DMA.

TABLE 5

ASCORBIC ACID INTERFERENCE RESISTANCE
Percent recovery, based on mg/dL ascorbic acid spikes

| mg/dL ascorbic acid -> | 0 | 6 | 12 | 25 | 50 |
|---|---|---|---|---|---|
| DMA | 100 | 103 | 90 | 83 | 61 |
| NENCEA | 100 | 99 | 102 | 101 | 100 |
| NMAP | 100 | 100 | 96 | 96 | 95 |
| NMNCEA | 100 | 100 | 95 | 97 | 97 |
| NEAP | 100 | 96 | 91 | 93 | 88 |
| PAPA | 100 | 93 | 95 | 92 | 92 |

Table 3 shows the molar absorptivity of selected dyes according to the present invention.

TABLE 6

| Molar Absorptivity of selected dyes | |
|---|---|
| | Molar absorptivity (E) |
| NENCEA | 62,000 |
| PAPA | 51,000 |
| NEAP | 42,000 |
| NMAP | 41,000 |
| NMNCEA | 28,000 |

The color-forming couplers have many features which enable them to form dyes with hydrazones or aminoantipyrines which are superior to dyes currently available. The couplers of the present invention form colored dyes which have high molar absorptivities at or near neutral pH. The dyes formed are highly water soluble, which makes them particularly useful for preparing dry chemistry reagent strips.

The color-forming couplers contain functional groups that make them easily immobilizable onto solid support matrices such as cellulose, silica and the like, for use in solid phase diagnostic devices.

Of particular importance in preparing assays for long-term monitoring of patients who may be taking vitamin C supplements, the dyes formed by the couplers of the present invention show high resistance to interference from ascorbic acid.

Unlike commercially available dyes whose color derives from the aniline residue of the dye molecule, but whose immobilizable functional group is not a coincidental part of the color-forming moiety, the immobilizable functional groups of the dyes formed according to the present invention are coincident with the chromophoric moiety.

Any recitation of a preferred range is to be deemed to include a description of the included subranges. Any recitation of a multimember class of elements is to be deemed to include a description of the possible subclasses. Any recitation of individual embodiments is to be deemed to also include a description of all possible combinations of said embodiments. All references, including prior patent applications cited (if any), are to be deemed incorporated by reference.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A dye forming composition which forms a color in the presence of hydrogen peroxide comprising a first compound, said first compound selected from the group consisting of:

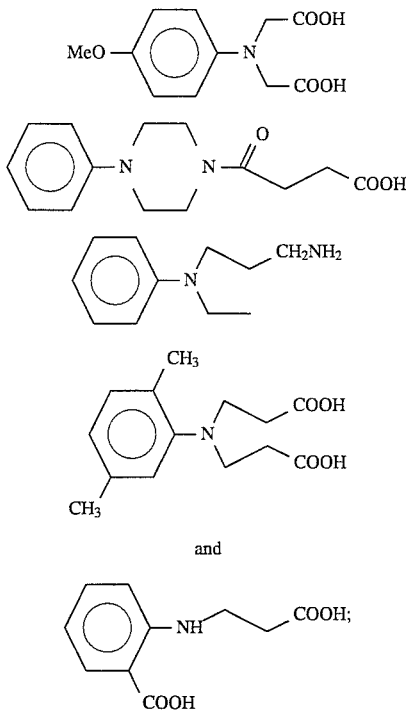

and a second compound selected from the group consisting of hydrazones and 4-aminoantipyrines.

2. The dye forming composition according to claim 1 wherein said second compound is a hydrazone.

3. The composition according to claim 2 wherein the hydrazonea have formula:

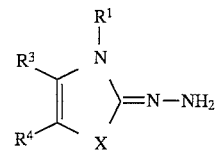

wherein $R^1$ is $C_{1-4}$ alkyl; X is S, O or $NR^2$; $R^2$ is $C_{1-4}$ alkyl; and $R^1$ and $R^2$ may be the same or different;

$R^3$ and $R^4$ are phenyl, pyridinyl, naphthyl, or quinolinodyl and may be the same or different, or $R^3$ and $R^4$ together form a fused benzene, pyridine, naphthalene, or quinoline ring;

and the saturated ring nitrogen is at a position vicinal to the hydrazone functional group.

4. The composition according to claim 2 wherein the hydrazone is selected from the group consisting of 3-methyl-2-benzothiazolinone hydrazone, 1-methyl-2-quinoline hydrazone, N-methyl-pyridone-4-hydrazone, N-methyl-pyridone-2-hydrazone, N-methyl-quinoline-2-hydrazone, N-methyl-quinoline-4-hydrazone, N-methyl-2-benzothiazolinone hydrazone, N-methyl-thiazolinone-2-hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone, 1,3-dimethyl-benzimidazolinone-2-hydrazone, and 3-($C_{1-4}$ alkyl)-2-benzothiazolinone hydrazone.

5. The dye forming composition according to claim 1 wherein said second compound is a 4-aminoantipyrine.

6. The composition according to claim 5 wherein the hydrazones have the formula:

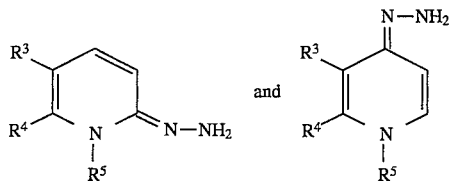

wherein $R^5$ is $C_{1-4}$ alkyl, $R^3$ and $R^4$ are phenyl, pyridinyl, naphthyl, or quinolidyl and $R^3$ and $R^4$ are the same of different, or $R^3$ and $R^4$ together form a fused benzene, pyridine, naphthalene or quinoline ring, and the saturated ring nitrogen is at a position ortho or para to the hydrazone functional group.

7. The composition according to claim 5 wherein the 4-aminoantipyrine is selected from the group consisting of 4-aminoantipyrine, 4-(dimethylamino)antipyrine, 4-(ethylamino)antipyrine, 4-(methylamino)antipyrine, 4-(sodium sulfonatomethylamino)antipyrine, 4-)sodiumsulfonatomethyl)(isobutyl)aminoantipyrine, 4-(sodium sulfonatomethyl)(methyl)amino antipyrine, and 4-(isopropyl) amino antipyrine.

8. In an assay device which comprises a support and a reagent layer having contained therein a color indicator composition for detecting hydrogen peroxide, the improvement wherein the color composition comprises a combination of a first compound of the formula:

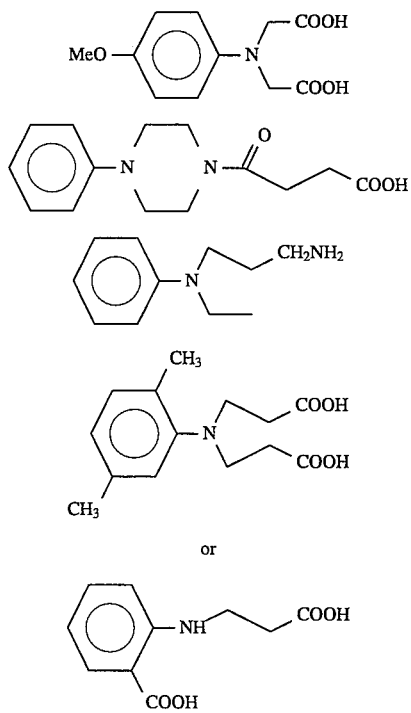

and a second compound selected from the group consisting of hydrazones and 4-aminoantipyrines.

9. The composition according to claim 8 wherein the hydrazones have the formula:

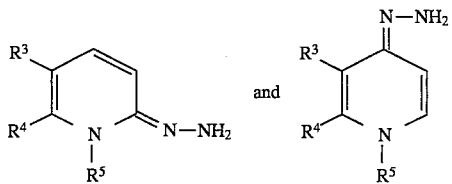

wherein $R^5$ is $C_{1-4}$ alkyl, $R^3$ and $R^4$ are phenyl, pyridinyl, naphthyl, or quinolidyl and $R^3$ and $R^4$ are the same or different, or $R^3$ and $R^4$ together form a fused benzene, pyridine, naphthalene or quinoline ring, and the saturated ring nitrogen is at a position ortho or para to the hydrazone functional group.

10. The assay device according to claims 8 wherein said second compound is a hydrazone.

11. The assay device according to claim 10 wherein the hydrazone is selected from the group consisting of 3-methyl-2-benzothiazolinone hydrazone, 1-methyl-2-quinoline hydrazone, N-methyl-pyridone-4-hydrazone, N-methyl-pyridone-2-hydrazone, N-methyl-quinoline-2-hydrazone, N-methyl-quinoline-4-hydrazone, N-methyl-2-benzothiazolinone hydrazone, N-methyl-thiazolinone-2-hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone, 1,3-dimethyl-benzimidazolinone-2-hydrazone, and 3-($C_1$–$C_4$ alkyl)-2-benzothiazolinone hydrazone.

12. The assay device according to claim 11 wherein the hydrazone has the formula:

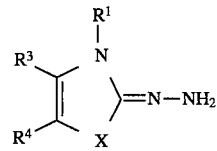

wherein $R^1$ is $C_{1-4}$ alkyl; X is S, O, or $NR^2$; $R^2$ is $C_{1-4}$ alkyl; and $R^1$ and $R^2$ may be the same or different;

$R^3$ and $R^4$ are phenyl, pyridinyl, naphthyl, or quinolinodyl and may be the same or different, or $R^3$ and $R^4$ together form a fused benzene, pyridine, naphthalene, or quinoline ring;

and the saturated ring nitrogen is at a position vicinal to the hydrazone functional group.

13. The assay device according to claim 8 wherein said second compound is a 4-aminoantipyrine.

14. The assay device according to claim 13 wherein the 4-aminoantipyrine is selected from the group consisting of 4-aminoantipyrine, 4-(dimethylamino)antipyrine, 4-(ethylamino)antipyrine, 4-(methylamino)antipyrine, 4-(sodium sulfonatomethylamino)antipyrine, 4-(sodiumsulfonatomethyl) (isobutyl)aminoantipyrine, 4-(sodiumsulfonatomethyl) (methyl)amino antipyrine, and 4-(isopropyl) aminoantipyrine.

15. A method for determining hydrogen peroxide or an analyte which reacts to produce hydrogen peroxide in an aqueous liquid, said method comprising the steps of:

in the presence of a substance having peroxidative activity, physically contacting a sample of a liquid with a dye forming composition which forms a color in the presence of hydrogen peroxide, said dye forming composition comprising a first compound, said first compound selected from the group consisting of:

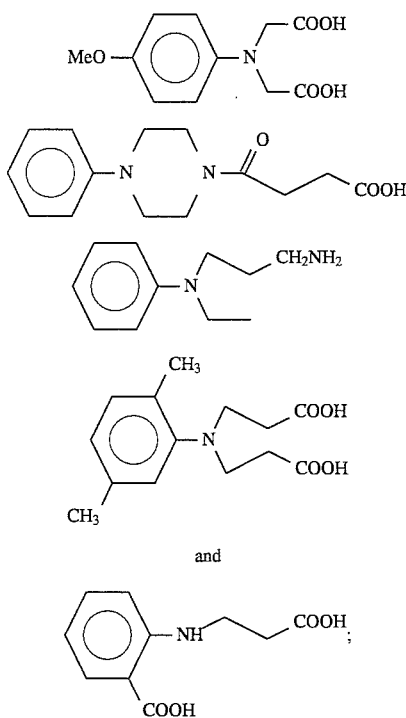

and

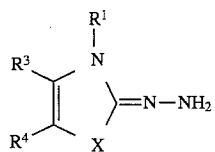

and a second compound selected from the group consisting of hydrazones and 4-aminoantipyrines.

16. The method according to claim 15 wherein the hydrazonea have the formula:

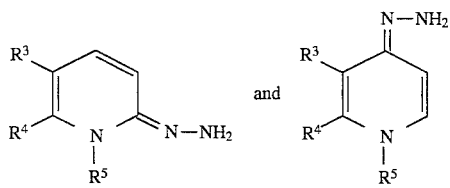

wherein $R^1$ is $C_{1-4}$ alkyl; X is S, O or $NR^2$; $R^2$ is $C_{1-4}$ alkyl; and $R^1$ and $R^2$ may be the same or different;

$R^3$ and $R^4$ are phenyl, pyridinyl, naphthyl, or quinolinodyl and may be the same or different, or $R^3$ and $R^4$ together form a fused benzene, pyridine, naphthalene, or quinoline ring;

and the saturated ring nitrogen is at a position vicinal to the hydrazone functional group.

17. The composition according to claim 15 wherein the hydrazones have the formula:

wherein $R^5$ is $C_{1-4}$ alkyl, $R^3$ and $R^4$ are phenyl, pyridinyl, naphthyl, or quinolidyl and $R^3$ and $R^4$ are the same or different, or $R^3$ and $R^4$ together form a fused benzene, pyridine, naphthalene or quinoline ring, and the saturated ring nitrogen is at a position ortho or para to the hydrazone functional group.

18. The method according to claim 15 wherein said analyte is cholesterol and said contacting step occurs in the presence of cholesterol oxidase.

19. The method according to claim 15 wherein said analyte is cholesterol and said contacting step occurs in the presence of glucose oxidase.

20. The method according to claim 15 wherein said second compound is a hydrazone.

21. The method according to claim 20 wherein the second compound is selected from the group consisting of 3-methyl-2-benzothiazolinone hydrazone, 1-methyl-2-quinoline hydrazone, N-methyl-pyridone-4-hydrazone, N-methyl-pyridone-2-hydrazone, N-methyl-quinoline-2-hydrazone, N-methyl-quinoline-4-hydrazone, N-methyl-2-benzothiazolinone hydrazone, N-methyl-thiazolinone-2-hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone, 1,3-dimethyl-benzimidazolinone-2-hydrazone, and 3-($C_1$-$C_4$ alkyl)-2-benzothiazolinone hydrazone.

22. The method according to claim 15 wherein said second compound is a 4-aminoantipyrine.

23. The method according to claim 22 wherein the second compound is selected from the group consisting of 4-aminoantipyrine, 4-(dimethylamino)antipyrine, 4-(ethylamino)antipyrine, 4-(methylamino)antipyrine, 4-(sodium sulfonatomethylamino)antipyrine, 4-(sodiumsulfonatomethyl) (isobutyl)amino antipyrine, and 4-(sodium sulfonatomethyl)(methyl)amino antipyrine, and 4-(isopropyl) amino antipyrine.

24. The method according to claim 15 wherein said sample contains ascorbic acid.

25. The method according to claim 24 wherein said sample contains at least 5 mg/dL ascorbic acid.

26. A diagnostic test kit for the determination of hydrogen peroxide, said kit comprising a container means containing:

a dye forming composition which forms a color in the presence of hydrogen peroxide comprising a first compound, said first compound selected from the group consisting of:

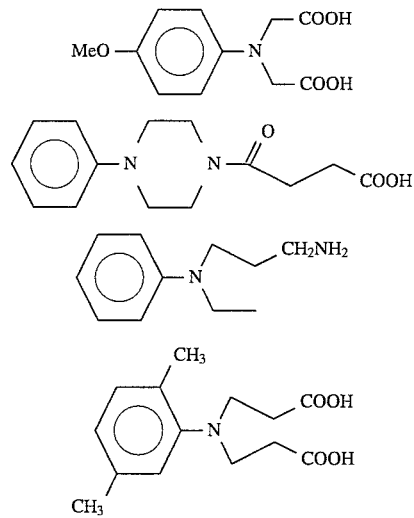

and

-continued

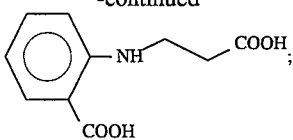

and a second compound selected from the group consisting of hydrazones and 4-aminoantipyrines.

27. The diagnostic test kit according to claim 26 wherein the hydrazonea have the formula:

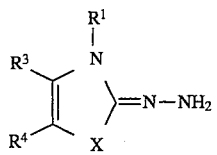

wherein $R^1$ is $C_{1-4}$ alkyl; X is S, O or $NR^2$; $R^2$ is $C_{1-4}$ alkyl; and $R^1$ and $R^2$ may be the same or different;

$R^3$ and $R^4$ are phenyl, pyridinyl, naphthyl, or quinolinodyl and may be the same or different, or $R^3$ and $R^4$ together form a fused benzene, pyridine, naphthalene, or quinoline ring;

and the saturated ring nitrogen is at a position vicinal to the hydrazone functional group.

28. The diagnostic test kit according to claim 26 wherein the hydrazones have the formula:

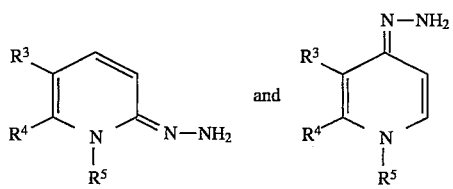

wherein $R^5$ is $C_{1-4}$ alkyl, $R^3$ and $R^4$ are phenyl, pyridinyl, naphthyl, or quinolidyl and $R^3$ and $R^4$ are the same or different, or $R^3$ and $R^4$ together form a fused benzene, pyridine, naphthalene or quinoline ring, and the saturated ring nitrogen is at a position ortho or para to the hydrazone functional group.

29. The diagnostic kit according to claim 26 wherein said second compound is a hydrazone.

30. The diagnostic kit according to claim 29 wherein the second compound is selected from the group consisting of 3-methyl-2-benzothiazolinone hydrazone, 1-methyl-2-quinoline hydrazone, N-ethyl-pyridone-4-hydrazone, N-methyl-pyridone-2-hydrazone, N-methyl-quinoline-2-hydrazone, N-methyl-quinoline-4-hydrazone, N-methyl-2-benzothiazolinone hydrazone, N-methyl-thiazolinone-2-hydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone, 1,3-dimethyl-benzimidazolinone hydrazone. benzothiazolinone hydrazone.

31. The diagnostic kit according to claim 26 wherein said second compound is a 4-aminoantipyrine.

32. The diagnostic kit according to claim 31 wherein the 4-aminoantipyrine is selected from the group consisting of 4-aminoantipyrine, 4-(dimethylamino)antipyrine, 4-(ethylamino)antipyrine, 4-(methylamino)antipyrine, 4-(sodium sulfonatomethylamino)antipyrine, 4-(sodiumsulfonatomethyl)(isobutyl)aminoantipyrine, 4-(sodium sulfonatomethyl)(methyl)amino antipyrine, and 4-(isopropyl) amino antipyrine.

* * * * *